| United States Patent [19] | [11] Patent Number: 5,055,493 |
|---|---|
| Leder | [45] Date of Patent: Oct. 8, 1991 |

[54] ANTIMICROBIAL COMPOSITION AND METHOD OF USE IN OIL WELL FLOODING

[75] Inventor: Jonathan Leder, Flemington, N.J.

[73] Assignee: Union Carbide Chemicals and Plastics Technology Corporation, Danbury, Conn.

[21] Appl. No.: 251,361

[22] Filed: Sep. 30, 1988

[51] Int. Cl.$^5$ ............................................ A01N 33/24
[52] U.S. Cl. .................................................. 514/727
[58] Field of Search ........................................ 514/727

[56] References Cited

U.S. PATENT DOCUMENTS

| 3,024,192 | 3/1962 | Bennett et al. |
| 3,558,788 | 1/1971 | Clark et al. |
| 3,592,893 | 7/1971 | Nosler et al. |
| 3,658,921 | 4/1972 | Wessendorf |
| 3,711,561 | 1/1973 | Wessendorf |
| 4,723,044 | 2/1988 | Watanabe et al. |
| 4,732,905 | 3/1988 | Donofrio et al. |

FOREIGN PATENT DOCUMENTS

| 53-118527 | 10/1978 | Japan |
| 63-93750 | 4/1988 | Japan |

OTHER PUBLICATIONS

Mitsui et al, Chem. Abst. vol. 110 (1989), p. 207,818h.
Kojima et al, Chem. Abst. vol. 90 (1979) p. 82146x.
Watanabe et al, Chem. Abst. vol. 106 (1987) p. 137,930e.
Ishii et al, Chem. Abst. vol. 109 (1988), p. 169,857q.
Ruseska et al, Technology, Oil and Gas Journal (Mar. 8, 1982) pp. 253–264.
Bowman et al, Antimicrobial Agents and Chemotherapy, vol. 2 No. 6 (Dec. 1972) pp. 504–505.
Journal of Medicinal Chemistry, vol. 17 No. 9 (1974) pp. 977–981.
Stott, J. F. D., et al., *Journal of Applied Bacteriology*, 1986, 60, pp. 57–66.
Maxwell, S., et al., "Biocide Application and Monitoring in a Waterflood System", pp. 209–218.
Lunden, K. C. et al., *Corrosion 85*, Paper No. 296, "Sulfate Reducing Bacteria in Oil and Gas Production", Mar. 25–29, 1985, Boston, MA.
Blackburn, F. E., *Corrosion 85*, Paper No. 289, "Detection, Monitoring, and Control of Bacterial Corrosion in a Large Middle-Esat Oilfield Waterflood", Mar. 25–29, 1985, Boston, MA.
Spoerner, T W., et al., *Corrosiion 86*, Paper No. 127, "Mothballing for Bacterial Control in Oilfied Waterflood and Producing Facilities" Mar. 17–21, 1986, Houston, TX.
Dewar, E. J., *Corrosion 86*, Paper No. 128, "Control of Microbiologically-Induced Corrosion and Solids Accumulation in a Seawater Flood System", Mr. 17–21, 1986, Houston, TX.
Costerton, J. W., et al., *Corrosion 87*, Paper No. 54, "Bacterial Biofilms in Relation to Internal Corrosion Monitoring and Biocide Strategies", Mar. 9–13, 1987, San Francisco, CA.
Smith, J. P., et al, *Corrosion 87*, Paper No. 366, "Biocide Selection and Optimization in Iiapco's Seawater Injection Project", Mar. 9–13, 1987, San Francisco, CA.
Sanders, P. F., et al., *Corrosion 87*, Paper No. 367, "Assessment, Monitoring and Control of Microbiological Corrosion Hazards in Offshore Oil Production Systems", Mar. 9–13, 1987, San Francisco, CA.
Pope, D. H., et al., *Corrosion 88*, Paper No. 249, "Methods for the Investigation of Under-Deposit Microbiologically Influenced Corrosion", Mar. 21–1988, St. Louis, MO.

*Primary Examiner*—Sam Rosen
*Attorney, Agent, or Firm*—Paul W. Leuzzi, II

[57] ABSTRACT

Antimicrobial compositions, containing 2,2-dibromo-2-nitroethanol, are fast acting and more effective than other halonitroalknaols, while particularly effective in industrial cooling water, pulp and paper manufacture, and for inhibiting sulfur-reducing bacteria growth in oil and gas well recovery.

9 Claims, No Drawings

ANTIMICROBIAL COMPOSITION AND METHOD OF USE IN OIL WELL FLOODING

FIELD OF THE INVENTION

This invention relates in general, to an antimicrobial composition and to a method of use. In one aspect, this invention relates to an antimicrobial composition containing a highly active microbiocide which is useful for a variety of applications including water treatment, pulp and paper manufacture and oil field water flooding. In a further aspect, this invention is directed to an antimicrobial composition containing 2,2-dibromo-2-nitroethanol as the major active biocide.

BACKGROUND OF THE INVENTION

Microbiocides are commonly used to control the growth of microorganisms in various industrial products and processes, including cooling water, paper manufacturing, oil field flood water, consumer products and the like. While a number of microbiocides are currently available, none is completely effective in all situations, and may also have undesirable characteristics in terms of handling, toxicology, spectrum of activity, cost and the like.

Chemical compounds which contain a geminal halonitro moiety are known to be bactericidal and fungicidal as reported by W. R. Bowman and R. J. Stretton, "Antimicrobial Activity of a Series of Halo-Nitro Compounds," *Antimicrobial Agents and Chemotherapy*, 2: 504–505 (1972, and N. G. Clark, B. Croshaw, B. E. Leggetter, and D. F. Spooner, "Synthesis and Antimicrobial Activity of Aliphatic Nitro Compounds," *J. Med. Chem.*, 17: 977–981 (1974).

A wide variety of these geminal halonitro compounds has been synthesized and tested for antimicrobial activity. While none shows activity which is outstanding in comparison to the rest of the group, the most effective compound has generally been found to be 2-bromo-2-nitro-1,3-propanediol. This compound has been commercialized under the name "Bronopol", and has been widely used in various fields where an antimicrobial agent is needed.

As indicated above, one such field where antimicrobial agents are particularly useful is in the oil and gas industry. For example, in United Kingdom Patent Application GB 2 183 477 A which was published June 10, 1987, novel solid antibacterial compositions are described which are indicated to be suitable for use in oil or gas wells against sulfate-reducing bacteria. These compositions were indicated to be solid nitroalkanols with 2-bromo-2-nitropropane-1,3-diol being preferred.

It is known that corrosion can occur in pipelines from oil wells due to the production of acids associated with the growth of bacterial colonies, particularly colonies of sulfate reducing bacteria. These colonies can develop in water in the presence of oil and can infect the entire well system.

It is also indicated in this application that a similar problem can exist in the collection of natural gases. Droplets of water can form on the interior of the gas pipe where colonies of bacteria can grow and give rise to corrosive conditions.

Thus, in the recovery of natural gases and in oil wells which utilize flooding operations, it is customary to employ an antibacterial compound to prevent or at least minimize corrosion. The reference further indicates that known compounds and methods using antibacterial compounds to inhibit bacterial growth are not entirely satisfactory. Any compounds used, must have a high degree of antibacterial activity against sulfate-reducing bacteria, such as, *Desulfovibrio desulfuricans.*

The novelty of the invention disclosed in this reference appears to reside in the utilization of the nitroalkanols as a solid carrier which will dissolve, disintegrate or disperse in water but not in oil. The nitroalkanols can rapidly pass through the oil layer in a well and locate in the denser water layer where the bacteria are located.

Although the United Kingdom reference acknowledges the absence in the literature of known compounds which are satisfactory as antibacterial agents for this particularly application, and proposes the nitroalkanols as overcoming the deficiency, none of the other compounds disclosed is indicated to possess unexpected properties, although bronopol is considered to be the preferred compound. Accordingly, it appears that the inventors have equated all of the members of the disclosed class as being substantially equivalent for the intended purpose.

Also in U.S. Pat. No. 3,024,192, which issued Mar. 6, 1962 to E. O. Bennett et al there is disclosed an improved method in a flooding program for the recovery of oil from oil bearing subterranean formations, which utilize a halonitroalkanol such as 2-bromo-2-nitro-1,3-propandiol, 2-chloro-2-nitro-1-butanol and the like.

Accordingly, one or more of the following objects will be achieved by the practice of the present invention. It is an object of this invention to provide a microbiocidal composition which is effective at relatively low concentrations of the active ingredient. Another object of this invention is to provide a microbiocidal composition which is effective rapidly and can be used in a wide variety of applications. A still further object of this invention is to provide a microbiocidal composition which contains as a major active ingredient, 2,2-dibromo-2-nitroethanol. Another object is to provide a method for killing or inhibiting the growth of organisms in industrial water cooling systems. It is also an object of this invention to provide a method for killing or inhibiting the growth of organisms in processes used in the production of pulp and paper. A still further object of this invention is to provide methods of using the novel compositions in the treatment of a wide variety of organisms. A further object is to provide a microbiocidal composition which is useful as a fuel preservative. Another object is to provide a method for killing or inhibiting the growth of sulfate-reducing bacteria which cause corrosion in the metal works of oil and gas collection systems. These and other objects will readily become apparent to those skilled in the art in the light of the teachings herein set forth.

SUMMARY OF THE INVENTION

In its broad aspect, the invention relates to an antimicrobial composition containing as an active ingredient, 2,2-dibromo-2-nitroethanol, hereinafter also referred to as "DBNE". The invention also relates to the use of the composition in various fields of application, particularly in oil field flooding operations and industrial cooling water treatment wherein a high degree of microbiocidal activity is needed in a relatively short period of time.

DETAILED DESCRIPTION OF THE INVENTION

As indicated above, it was known in the prior art that nitroalkanols were useful as antimicrobial agents. However, of this class of compounds, there was no recognition in the literature that any particular member of the nitroalkanols other than bronopol possessed any unexpected or surprising properties.

Accordingly, it has now unexpectedly and surprisingly been found that 2,2-dibromo-2-nitroethanol (DBNE) is a highly active antimicrobial agent, and when present in the antimicrobial composition even as the sole active ingredient it is vastly superior to other halonitroalkanols of the type disclosed in the literature including bronopol.

In a study of the activity of bronopol, it was discovered that a crude grade of bronopol had microbiocidal activity which was substantially greater than that of pure grades of bronopol. Chromatographic analysis of the product revealed the presence of an impurity which was present at low levels. Upon isolation, this material was characterized by chemical and spectroscopic methods and identified as DBNE. Further investigation revealed that this compound showed microbiocidal activity which is far superior to that of bronopol, particularly when measured after a brief contact of the microbiocide with microorganisms. In some instances, as hereinafter shown, the compound had complete kill against certain organisms while Bronopol was essentially ineffective. Thus, prior to the present invention, no one recognized that this particular halonitroalkanol possessed unexpected antimicrobial activity.

It was therefore surprising to find that when DBNE is employed in an antimicrobial composition as the major antimicrobial agent, such compositions offer superior activity than the halonitroalkanols of the prior art.

In practice, DBNE may be employed in antimicrobial compositions as the sole biocide or in combination with other biocides, including other halonitroalkanols. Thus, the antimicrobial composition of the present invention can be comprised of:

(A) an antimicrobially-effective amount of at least one biocide selected from the group consisting of:
 (a) 2,2-dibromo-2-nitroethanol,
 (b) 2,2-dibromo-2-nitroethanol and at least one other halonitroalkanol biocide, and
 (c) 2,2-dibromo-2-nitroethanol and at least one other biocide which is a non-halonitroalkanol biocide,
with the proviso that when biocide (b) is present, 2,2-dibromo-2-nitroethanol comprises at least about 10 weight percent of the total active biocide; and (B) an antimicrobially acceptable carrier.

When the composition consists essentially of DBNE, it can be present in a concentration of from about 0.5 to about 99 weight percent based on the total weight of the antimicrobial composition. When employed with other biocides which are not halonitroalkanols, DBNE can be present in an amount of from about 1 to about 99 weight percent, and more preferably from about 1 to about 10 weight percent, and more preferably at least 50 weight percent of the total biocidally active halonitroalkanol ingredients.

Among the other biocidally active ingredients which can be used in combination with DBNE are included compounds such as glutaraldehyde, isothiazolines, methylene-bis(thiocyanate), 2,2-dibromo-3-nitrilopropionamide, quaternary ammonium compounds, and the like.

As indicated, the antimicrobial composition of the present invention is comprised of DBNE as at least one of the biocidally active components and a biocidally acceptable carrier. The carriers can be inorganic or organic, and can be a solid or a liquid diluent in which DBNE is dissolved or dispersed. Since DBNE is soluble in water up to about 6 to 8 percent, the antimicrobial composition can be in the form of an aqueous solution. For other concentrations of DBNE, the carriers can include, but are not limited to, organic compounds, such as, hydrocarbons, halocarbons, including dichloromethane, alcohols, glycols, aldehydes, ketones, high molecular weight glycols, and the like, and inorganic compounds, such as, diatomaceous earth, pumice, and the like. Blending of the carrier and the biocidially active ingredients can be effected using conventional materials handling equipment by techniques known in the art.

The active component used in the present invention, 2,2-dibromo-2-nitroethanol, is conveniently prepared by one of several methods disclosed in the literature. For example, in U.S. Pat. No. 3,711,561 which issued Jan. 16, 1973 to R. Wessendorf of Germany, there is disclosed a process for preparing bromonitro alcohols of the formula:

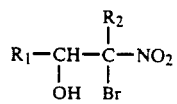

wherein $R_1$ is hydrogen, methyl or halogenated methyl and $R_2$ is hydrogen, methyl and ethyl which may be substituted with at least one hydroxy group such as

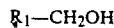

The alcohols of the indicated formula are prepared by reacting an aldehyde of the formula:

wherein $R_1$ is as indicated above, with a nitroalkanol of the formula:

wherein $R_3$ is hydrogen, methyl and ethyl and an alkali metal hydroxide. The aqueous solution of the metal alkali salt of the nitroalcohol is then reacted with bromine.

Depending upon the ratio of aldehyde and nitroalcohol employed, monohydroxy compounds or diols can be obtained. Thus for example, by reacting nitromethane with one equivalent of formaldehyde, followed by bromination, 2,2-dibromo-2-nitroethanol can be obtained.

A process for producing dibromonitro compounds is also disclosed in U.S. Pat. No. 4,723,044 which issued Feb. 2, 1988 to M. Watanabe et al and is assigned to Permachem Asia Ltd. of Tokyo, Japan. The reaction disclosed therein comprises condensing nitromethane with formaldehyde or acetaldehyde in the presence of alkali. The amount of alkali is at least 1.5 moles per mole of nitromethane. Thereafter, without isolating the product, the reaction mixture is treated with bromine, and the dibromonitro compound recovered.

As indicated above, the compositions of the present invention are effective against a wide variety of microorganisms. In practice, the composition containing DBNE will be employed in an "antimicrobially effective amount". By this term as employed throughout the specification and appended claims is meant that amount which is effective to kill at least 90 percent of the microorganisms with which it comes in contact, or to inhibit their growth as compared to similar but untreated systems. In general the amount of the composition will vary depending upon whether it is utilized in solid, liquid or a dispersed form.

In practice, the antimicrobial compositions will be employed in concentrations sufficient to provide from about 0.5 to about 1000 ppm, and more preferably from about 2 to about 100 ppm, of the active biocidal ingredients in the fluids being treated. Amounts above and below these ranges can be employed and will, of course, depend upon the individual circumstances.

The antimicrobial compositions of the present invention are effective against a broad spectrum of microorganisms including Gram-positive and Gram-negative bacteria, yeasts, fungi, molds and algae. The compositions are fast acting and are tens to hundreds of times more effective than bronopol, a preferred halonitroalkanol as disclosed in the prior art.

Illustrative microorganisms which can be effectively treated with the antimicrobial compositions of this invention, include, but are not limited to, the following:

Bacteria (Gram-positive or Gram-negative)

*Pseudomonas aeruginosa*
*Pseudomonas fluorescens*
*Staphylococcus aureus*
*Escherichia coli*
*Desulfovibrio desulfuricans*
*Legionella pneumophila*

Yeasts

*Candida albicans*
*Saccharomyces cerevisiae*

Molds

*Aspergillus niger*
*Cephalosporium acremonium*
*Penicillium notatum*
*Aureobasidium pullulans*

Algae

*Chlorella vulgaris*
*Euglena gracilis*
*Selenastrum capricornutum*

The compositions are also effective in a very short period of time after contact with the microorganism. Rapid kill of microorganisms is particularly important in industrial processes in which contact between biocide and microorganism is relatively brief. Examples of such processes include (1) treatment of cooling water and paper mill slurries (including white water), in which part of the water is periodically removed and replaced with fresh water, so that biocide is lost within several hours of its addition; (2) sugar processing and oil field water flooding, in which biocide is used in a "once-through" system, with a contact time of typically 15 minutes to 4 hours; and (3) hard surface disinfection in which the disinfectant is in contact with the surface for less than about 10 minutes.

In addition to the speed of kill, extent of kill in long-term contact situations is also important in many processes. Examples include (1) preservation of fuels, paints, slurries and consumer products; and (2) control of microorganisms in recirculating industrial fluids, such as metal working fluids and closed loop cooling water systems.

In the examples which follow, the effectiveness of DBNE was demonstrated by comparison with bronopol and glutaraldehyde against a variety of microorganisms.

In these examples specific strains were selected to be representative of various types of microorganisms and included the following:

| Organism | Type |
| --- | --- |
| *Pseudomonas aeruginosa* (Ps. aeruginosa) | Gram-negative bacteria |
| *Staphylococcus aureus* (St. aureus) | Gram-positive bacteria |
| *Candida albicans* (C. albicans) | Yeast |
| *Aspergillus niger* (A. niger) | Mold (vegetative) |
| *Aspergillus niger* (A. niger) | Mold (spores) |
| *Chlorella* sp. | Algae |
| *Desulfovibrio desulfuricans* | Sulfate-reducing bacteria |

EXAMPLES 1–10

DBNE vs Bacteria, Yeasts and Fungi (vegetative and spore forms)

In these examples, pure known strains of microorganisms were used for testing the general effectiveness of microbiocides.

A small portion of a pure stock culture was streaked on nutrient agar of the appropriate type (Table I) and allowed to grow. A single resulting colony was streaked on a fresh agar plate via serological loop. This procedure was repeated once more prior to use of the microorganisms in microbibiocide experiments.

The final plate or broth culture was allowed to grow for the appropriate time period (Table I) and was then harvested for use.

TABLE I

| Organism (ATCC#) | Media* | Incubation |
| --- | --- | --- |
| *Ps. aeruginosa* (15442) | BHI agar | 24 hours |
| *St. aureus* (6538) | BHI agar | 24 hours |
| *A. niger*, hyphae (16404) | PD broth | 8 days (shaken) |
| *A. niger*, spores (16404) | PD agar | 8 days |
| *C. albicans* (10231) | YM agar | 24 hours |

American Type Culture Collection
*BHI = Brain Heart Infusion
PD = Potato Dextrose
YM = Yeast Malt Extract Plates were harvested by adding 10 ml of sterile saline, agitating gently, and removing the resulting cell suspension with a sterile syringe. This suspension was diluted with sterile saline to produce an inoculum containing approximately $10^8$ cfu/ml of this suspension (0.1 ml) was used to inoculate each tube in the experiments described below.

Spore plates were harvested by a similar procedure, except that approximately 10 ul of nonionic surfactant was added to the saline used to flood the plate.

Fungal hyphae, (i.e., vegetative cells) were harvested by homogenizing the entire broth culture. The resulting mixture was then used as the inoculum without further processing. This suspension (500ul) was used to inoculate each tube in the experiments described below.

The biocides were serially diluted into tubes containing 10 ml of 0.1 M phosphate buffer at pH 7. In addition, one tube contained no biocide, to serve as a control.

An inoculum of the appropriate size (described above) was added to each tube, which were allowed to stand at room temperature. Aliquots were removed after 1,3,7, and 24 hours and counted by pour plating of serial dilutions.

Minimum cidal concentrations (MCCs) are defined as the minimum concentration of a biocide (in ppm a.i.) which was sufficient to yield no detectable growth of a given microorganism at a given contact time. The results obtained after 1 and 24 hours contact time, respectively, are set forth in Tables II and III below.

TABLE II

Comparison with Bronopol and Glutaraldehyde
1 Hour MCCs*

| Example | Microorganism | DBNE | Bronopol | Glutaraldehyde |
|---|---|---|---|---|
| 1 | A | 4 | >>70 | 50 |
| 2 | B | >32 | >>80 | >50 |
| 3 | C | 32 | >>128 | >>100 |
| 4 | D | 32 | >>512 | >>100 |
| 5 | E | 64 | >>1024 | >>1024 |

A - Ps. aeruginosa
B - St. aureus
C - C. albicans
D - A. niger (vegetative)
E - A. niger (spores)
*ppm a.i. (active ingredient)
> means that complete kill was not achieved at the highest concentration tested but that microbial populations were reduced by at least 99%.
>> means that no reduction in microbial populations was achieved at the highest concentration tested.

TABLE III

Comparison with Bronopol and Glutaraldehyde
24 Hour MCCs

| Example | Microorganism | DBNE | Bronopol | Glutaraldehyde |
|---|---|---|---|---|
| 6 | A | 2 | 8 | 50 |
| 7 | B | <1 | 80–160 | 10 |
| 8 | C | <4 | <128 | <100 |
| 9 | D | 8 | <512 | >100 |
| 10 | E | 16 | 64 | 500 |

A - Ps. aeruginosa
B - St. aureus
C - C. albicans
D - A. niger (vegetative)
E - A. niger (spores)
> means that complete kill was not achieved at the highest concentration tested but that microbial populations were reduced by at least 99%.
< means that complete kill was achieved at the lowest concentration tested.

EXAMPLES 11–16

DBNE vs Sulfate Reducing Bacteria

*Desulfovibrio desulfuricans* Mid-continent A strain was inoculated into SRB vials and allowed to grow for 1 week to provide an inoculum. Two days prior to biocide challenge, a 0.1 ml aliquot of this inoculum was added to fresh test vials, and these vials were allowed to grow at 37° C. for two days to provide mixtures containing $10^{7-8}$ cells per ml. Immediately prior to biocide challenge, the test vials were purged of excess hydrogen sulfide by bubbling with argon for approximately 90 seconds. The biocides were then added to provide concentrations of 1, 5, 10, 25, 50, 100, 250, and 500 ppm active ingredient. In addition, one vial contained no biocide to serve as a control. All tests were run in duplicate. Aliquots (0.1 ml) were removed from each vial after 1 hour and subcultured into fresh SRB vials, which were placed in an incubator and observed for growth (measured as blackening of the vial) after 48 hours. The minimum cidal concentration reported is the minimum concentration of a given biocide which gave rise to no growth in the corresponding subculture vial.

The results are set forth in Table IV below.

TABLE IV

Comparison of DBNE With Commercial Biocides

| Example | Biocide | 1-Hour MCC (ppm active) |
|---|---|---|
| 11 | Acrolein | 50 |
| 12 | Thiocarbamate* | 500 |
| 13 | Cocodiamine acetate | 100 |
| 14 | DBNE | 5 |
| 15 | Glutaraldehyde | 50 |
| 16 | Quaternary ammonium** (ADBAC) | 50 |

Concentrations tested: 1, 5, 10, 25, 50, 100, 250, 500 ppm.
Test organism: *Desulfovibrio desulfuricans*, Mid-continent A strain.
*Thiocarbamate = mixture of sodium dimethyldithiocarbamate (15%) + disodium ethylene bis(dithiocarbamate) (15%).
**Quaternary ammonium compound = alkyl (68% C-12, 25% C-14, 7% C-16) dimethylbenzylammonium chloride.

EXAMPLES 17–19

DBNE vs Algae

A culture of Chlorella sp. was inoculated into 50 ml of sterile Bold's Basic Media (BBM) in a sterile shaker flask. The mixture was capped and allowed to grow under artificial sunlight at 20° C. in a gyrorotary shaker for 6 days. The resulting culture was used as inoculum in the test flasks below.

An appropriate amount of biocide was added to 45 ml of BBM in sterile test flasks to provide concentrations of each biocide as follows:

| Bronopol: | 5, 10, 20, 40, and 80 ppm. |
|---|---|
| DBNE: | 1, 2, 3, 4, and 5 ppm. |
| Glutaraldehyde: | 10, 20, 40, 80, and 160 ppm. |

The inoculum (1.0 ml) described above was then added to each flask, and the flasks returned to the lighted shaker for 5 days. After that time, the flasks were observed for growth (turbidity). The minimum inhibitory concentrations reported in Table V below are the lowest concentrations of the biocide which prevented growth in the flasks.

TABLE V

Comparison of Biocides vs Algae

| Example | Compound | Minimum Inhibitory Concentration |
|---|---|---|
| 17 | DBNE | 4 ppm |
| 18 | bronopol | 80 ppm |
| 19 | glutaraldehyde | 80 ppm |

The data presented in the preceding tables, show that after 1 hour of contact between the biocide and the microorganism, DBNE yields complete kill against all but *Staphylococcus aureus*, (the population of which was reduced by greater than 99%), while bronopol has essentially no effect on any of the organisms tested. After a 24 hour contact time, DBNE is from 4 times to greater than 100 times more efficacious than bronopol and provided complete kill even against Staphylococcus. Against algae, DBNE is 20 times more effective than bronopol.

Although the invention has been illustrated by the preceding examples, it is not to be construed as being limited to the materials employed therein, but rather, the invention relates to the generic area as herein before disclosed. Various modifications and embodiments thereof can be made without departing from the spirit or scope thereof.

What is claimed is:

1. A method of killing or inhibiting the growth of bacteria in a liquid employed in an oil well flooding operation which comprises contacting said liquid with a bactericidally effective amount of a composition comprised of at least one biocide selected from the group consisting of:
   (a) 2,2-dibromo-2-nitroethanol,
   (b) 2,2-dibromo-2-nitroethanol and at least one other halonitroalkanol biocide, and
   (c) 2,2-dibromo-2-nitroethanol and at least one other biocide which is a non-halonitroalkanol biocide,
with the proviso that when biocide (b) is present, 2,2-dibromo-2-nitroethanol comprises at least 10 weight percent of the total active biocide and the flooding said oil well with said liquid.

2. A method of inhibiting the growth of sulfate-reducing bacterial in oil and gas collection systems which comprises contacting said bacterial with an bactericidally effective amount of a composition comprised of at least one biocide selected from the group consisting of:
   (a) 2,2-dibromo-2-nitroethanol,
   (b) 2,2-dibromo-2-nitroethanol and at least one other halonitroalkanol biocide, and
   (c) 2,2-dibromo-2-nitroethanol and at least one other biocide which is a non-halonitroalkanol biocide,
with the proviso that when biocide (b) is present, 2,2-dibromo-2-nitroethanol comprises at least 10 weight percent of the total active biocide.

3. A method of killing or inhibiting the growth of bacteria in a liquid employed in an oil well flooding operation which comprises contacting said liquid with a bactericidally effective amount of a composition containing 2,2-dibromo-2-nitroethanol as the major active biocide and then flooding said oil well with said liquid.

4. A method of killing or inhibiting the growth of sulfate-reducing bacteria in oil and gas collection systems which comprises contacting said bacteria with a bactericidally effective amount of a composition containing 2,2-dibromo-2-nitroethanol as the major active biocide.

5. The method of claims 1 or 2 wherein said biocide is 2,2-dibromo-2-nitroethanol.

6. The method of claims 1 or 2 wherein 2,2-dibromo-2-nitroethanol is used in combination with at least one other biocide.

7. The method of claims 1,2,3 or 4 wherein said biocide is 2,2-dibromo-2-nitroethanol and at least one other biocide which is a non-halonitroalkanol biocide.

8. The method of claims 1,2,3 or 4 wherein said biocide is used in combination with an antimicrobially acceptable carrier.

9. The method of claim 5 wherein said biocide is present in said composition in an amount of from about 0.5 to about 99 weight percent.

* * * * *